United States Patent
Harding et al.

(10) Patent No.: US 9,207,154 B2
(45) Date of Patent: Dec. 8, 2015

(54) METHOD AND SYSTEM FOR CREEP MEASUREMENT

(71) Applicant: General Electric Company, Schenectady, NY (US)

(72) Inventors: Kevin George Harding, Niskayuna, NY (US); Yi Liao, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 109 days.

(21) Appl. No.: 14/059,491

(22) Filed: Oct. 22, 2013

(65) Prior Publication Data

US 2015/0107368 A1   Apr. 23, 2015

(51) Int. Cl.
| | |
|---|---|
| *G01L 1/24* | (2006.01) |
| *G01N 3/08* | (2006.01) |
| *G01D 5/347* | (2006.01) |
| *G01B 11/00* | (2006.01) |
| *G01B 11/16* | (2006.01) |

(52) U.S. Cl.
CPC *G01N 3/08* (2013.01); *G01B 11/00* (2013.01); *G01B 11/16* (2013.01); *G01B 11/165* (2013.01); *G01D 5/347* (2013.01); *G01L 1/246* (2013.01); *G01N 2203/0071* (2013.01); *G01N 2203/0647* (2013.01)

(58) Field of Classification Search
CPC ... G01M 15/14; G01M 13/00; G01M 5/0033; G01N 2203/0071; G01L 1/246
USPC .............. 73/112.01, 760, 788, 799, 800, 822, 73/862.621, 818, 826
See application file for complete search history.

(56) References Cited

U.S. PATENT DOCUMENTS

| | | | | |
|---|---|---|---|---|
| 4,026,660 | A * | 5/1977 | Ueda et al. ....................... 416/61 |
| 4,490,773 | A * | 12/1984 | Moffatt ....................... 361/283.4 |
| 4,591,996 | A * | 5/1986 | Vachon ............................ 702/42 |
| 4,649,759 | A * | 3/1987 | Lee ............................ 73/862.626 |
| 4,979,827 | A * | 12/1990 | Matsui ........................... 356/499 |
| 5,238,366 | A * | 8/1993 | Ferleger ........................... 416/61 |
| 5,436,462 | A | 7/1995 | Hull-Allen |
| 5,568,259 | A * | 10/1996 | Kamegawa .................... 356/625 |
| 6,259,111 | B1 * | 7/2001 | Tullis ......................... 250/559.32 |
| 6,817,528 | B2 | 11/2004 | Chen |

(Continued)

FOREIGN PATENT DOCUMENTS

JP       2011027526 A    2/2011

OTHER PUBLICATIONS

Wu et al., "Research on Color Space-Time Coded Structured Light for Molded Line Evaluation in Industrial Site", International Forum on Strategic Technology (IFOST), Oct. 13-15, 2010, pp. 1-4.

(Continued)

*Primary Examiner* — Lisa Caputo
*Assistant Examiner* — Jonathan Dunlap
(74) *Attorney, Agent, or Firm* — Paul J. DiConza

(57) ABSTRACT

A method and system for monitoring creep in an object are provided. The creep monitoring system includes a creep sensor assembly that includes at least one image pattern pair disposed on a surface of the object. The creep monitoring method includes receiving information from the creep sensor assembly regarding an observed creep and an offset associated with the object, correcting the observed creep using the information regarding the offset and outputting the corrected information relative to the creep.

16 Claims, 3 Drawing Sheets

(56) References Cited

U.S. PATENT DOCUMENTS

| | | | |
|---|---|---|---|
| 7,064,811 B2* | 6/2006 | Twerdochlib | 356/24 |
| 7,162,373 B1* | 1/2007 | Kadioglu et al. | 702/35 |
| 7,360,437 B2* | 4/2008 | Hardwicke et al. | 73/763 |
| 7,411,150 B2* | 8/2008 | Lavers et al. | 219/121.71 |
| 7,493,809 B1* | 2/2009 | Ward, Jr. | 73/168 |
| 7,552,647 B2* | 6/2009 | Soechting et al. | 73/802 |
| 7,690,840 B2* | 4/2010 | Zombo et al. | 374/121 |
| 7,787,996 B2* | 8/2010 | Draper et al. | 700/287 |
| 7,810,385 B1 | 10/2010 | Narcus | |
| 7,905,031 B1 | 3/2011 | Paulino | |
| 7,925,454 B1 | 4/2011 | Narcus | |
| 8,209,839 B1 | 7/2012 | Brostmeyer et al. | |
| 8,525,073 B2* | 9/2013 | Quitter et al. | 219/121.67 |
| 8,665,426 B2* | 3/2014 | Huettner et al. | 356/139.04 |
| 8,818,078 B2* | 8/2014 | Telfer et al. | 382/154 |
| 8,818,130 B2* | 8/2014 | Morgan-Mar et al. | 382/276 |
| 2003/0063270 A1* | 4/2003 | Hunik | 356/32 |
| 2005/0083032 A1* | 4/2005 | Goldfine et al. | 324/71.1 |
| 2007/0070327 A1* | 3/2007 | Asundi et al. | 356/32 |
| 2007/0120561 A1* | 5/2007 | Goldfine et al. | 324/238 |
| 2007/0258807 A1* | 11/2007 | Brummel | 415/118 |
| 2009/0178417 A1* | 7/2009 | Draper et al. | 60/783 |
| 2010/0030493 A1* | 2/2010 | Rao | 702/39 |
| 2011/0099809 A1* | 5/2011 | Hovel et al. | 29/888 |
| 2012/0166102 A1* | 6/2012 | Nieters et al. | 702/34 |
| 2012/0176629 A1 | 7/2012 | Allen et al. | |
| 2013/0057650 A1 | 3/2013 | Song et al. | |

OTHER PUBLICATIONS

Liao et al., "Continuous Turbine Blade Creep Measurement Based on Moiré", Optical Metrology and Inspection for Industrial Applications II, Proc. of SPIE, vol. 8563, Nov. 20, 2012, pp. 85630H-1-85630H-12.

* cited by examiner

METHOD AND SYSTEM FOR CREEP MEASUREMENT

BACKGROUND

The field of the invention relates generally to rotating machinery, and more specifically, to a system and method for creep measurement of rotating components.

As rotatable machines operate, a condition of components of the machine may deteriorate over time. This degradation of condition typically affects performance. Degradation may be due to various factors. One such factor is the deformation of the material of the component when exposed to stresses less than its yield strength over time, via a mechanism commonly referred to as creep. Creep can degrade gaps between parts that move relative to each other and can create projectile hazards and debris if the creep is permitted to occur until failure of the component material. Some components, such as turbine blades, are difficult or costly to remove from service for periodic inspections, and scheduled shutdowns for plant maintenance and repair may occur infrequently enough that creep may cause damage before it can be detected and repaired.

A method has been demonstrated to measure strain of rotating components such as turbine parts, using a periodic pattern printed on a part, compared against a referenced pattern to create a moiré pattern. In this method, the moiré pattern created is entirely assumed to be the result of the surface strain or creep of the part, without accounting for any miss-alignment, equipment change, or environmental changes. Hence, there is a need to separately recognize and correct the contribution of these factors in the creation of the moiré pattern, and thereby more accurately measure the actual creep that is undergone by the parts.

BRIEF DESCRIPTION

In one embodiment, a method of monitoring creep in an object is disclosed. The method includes monitoring a creep sensor assembly that has an image pattern pair disposed on a surface of the object, receiving information from the creep sensor assembly regarding an observed creep associated with the object, receiving information from the creep sensor assembly regarding an offset of the creep sensor assembly, correcting the observed creep using the information regarding the offset, and outputting the corrected information relative to creep. The image pattern pair of the creep sensor assembly includes a first pattern and a second pattern.

In another embodiment, a creep monitoring system for monitoring creep in an object is disclosed. The system includes a creep sensor assembly. The creep sensor assembly includes an image pattern pair including a first pattern and a second pattern disposed on a surface of the object. The creep sensor assembly further includes an optical monitoring system and a processor. The optical monitoring system is in line of sight to the image pattern pair, and configured to collect information regarding observed creep and an offset of the creep sensor assembly. The processor is configured to receive the information regarding the observed creep and the offset; and determine a corrected information relative to creep.

BRIEF DESCRIPTION OF THE DRAWINGS

These and other features, aspects, and advantages of the present invention will become better understood when the following detailed description is read with reference to the accompanying drawings, in which like characters represent like parts throughout the drawings, wherein.

DETAILED DESCRIPTION OF THE INVENTION

The following detailed description illustrates embodiments of the invention by way of example and not by way of limitation. It is contemplated that the invention has general application to analytical and methodical embodiments of monitoring creep in moving objects in industrial, commercial, and residential applications.

As used herein, an element or step recited in the singular and preceded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Embodiments of the present invention provide a creep monitoring system for high speed rotating devices, such as, but not limited to, a gas turbine blade. In various embodiments, a creep rate, a crack presence and size, a temperature, and a coating spallation for high speed rotating devices are monitored simultaneously. The creep monitoring system can be a part of a prognosis and health monitoring (PHM) system.

Figure 1:
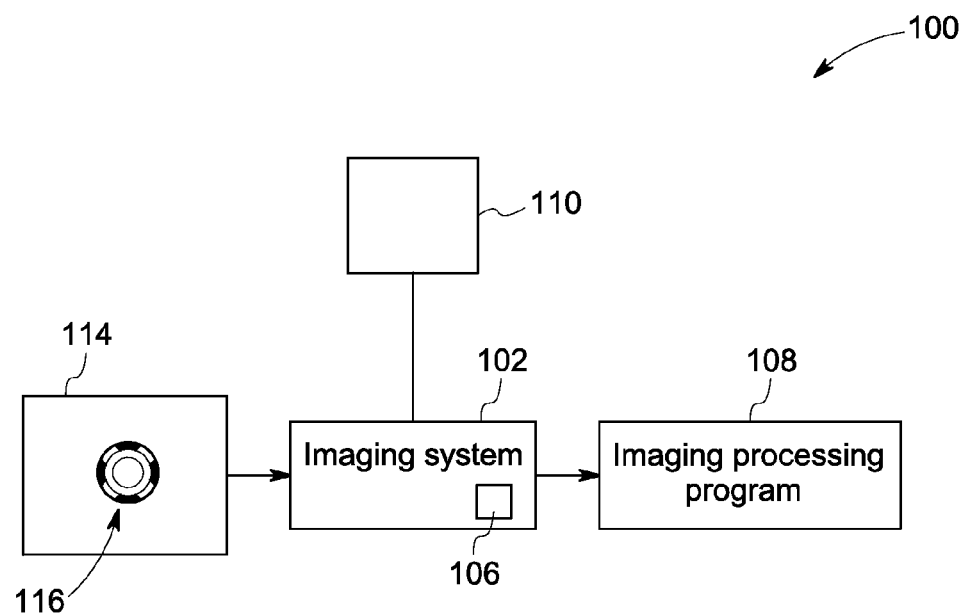
FIG. 1 is a schematic block diagram of a creep monitoring system, in accordance with an exemplary embodiment of the present invention.

FIG. 1 is a schematic block diagram of an exemplary creep monitoring system 100 that can be used for the creep measurement by creating a moiré pattern. In the exemplary embodiment, the creep monitoring system 100 includes at least one of an imaging system 102. The imaging system 102 includes a processor 106 configured to execute an image processing program 108 that directs the imaging system 102 to acquire images and/or image patterns from an imaging sensor 110 and analyze the images and/or image patterns for creep related calculations. The image pattern can be a moiré pattern, or other image patterns with fine features for creep calculation. Imaging system 102 may be configured to monitor a static or moving object 114. The object 114 may be a turbine blade, a fan or compressor blade, or other airfoil having a creep sensor assembly 116 formed thereon. In various embodiments, creep sensor assembly 116 includes imaging sensor 110 for use with imaging system 102.

Figure 2:
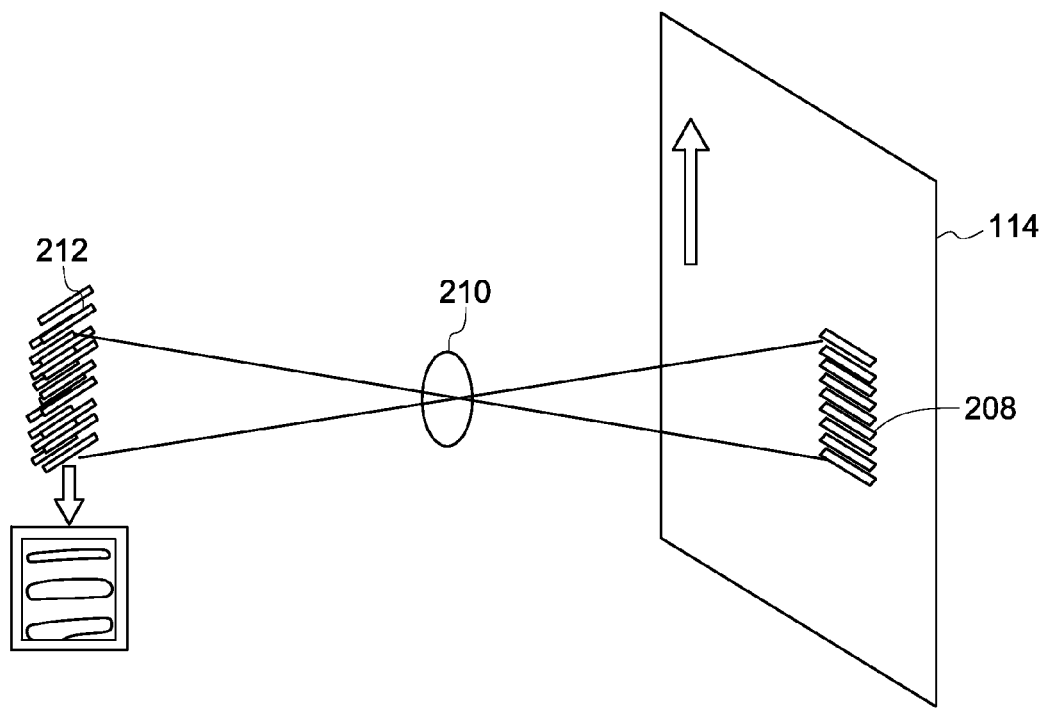
FIG. 2 is a schematic diagram of imaging a moiré pattern on an object, in accordance with an exemplary embodiment of the present invention.

FIG. 2 is a schematic diagram of imaging a moiré pattern on an object 114. In the exemplary embodiment, a moiré pattern 208 is positioned on object 114. Moiré pattern 208 is viewed through an optical monitoring system 210 that is in line of sight with the pattern 208. If object 114 has stretched, for example, due to creep, a moiré beat pattern 212 is observed and the amount of creep is determined from varying characteristics of moiré beat pattern 212. The characteristics such as, for example, frequency and interference patterns of the moiré beat pattern 212 would change with the change in frequency of the moiré pattern 208 due to creep.

Various manufacturing techniques may be used to form creep sensor assembly 116 (shown in FIG. 1) on a surface of object 114. In the exemplary embodiment, manufacturing techniques for directly deposited creep sensor assembly 116 include, for example, but not limited to, direct writing, screen printing, thermal spraying, and depositing by a water jet. The creep sensor assembly 116 may be embodied in a single layer or multi-layered structure. In a multilayered structure, the different layers of creep sensor assemblies 116 may provide one or more useful functions, including, for instance, to permit a thermal expansion of creep sensor assemblies 116 to substantially match a thermal expansion of object 114, to serve as thermal insulation, or to provide protection from abrasion or moisture.

Various materials may be used to form creep sensor assembly 116 (shown in FIG. 1) on a surface of object 114. In an illustrative embodiment, a material used to form creep sensor assembly 116 has at least one of the following characteristics: it may have a different emissivity than the substrate material; it may be electrically conductive; it may be doped with other materials for better image contrast or to form a temperature sensor; and/or it may be functional under a harsh environment. Example materials to form creep sensor assembly 116 would include, but not limited to, oxides of titanium, aluminum, chromium, silicon, and yttrium.

Figure 3:
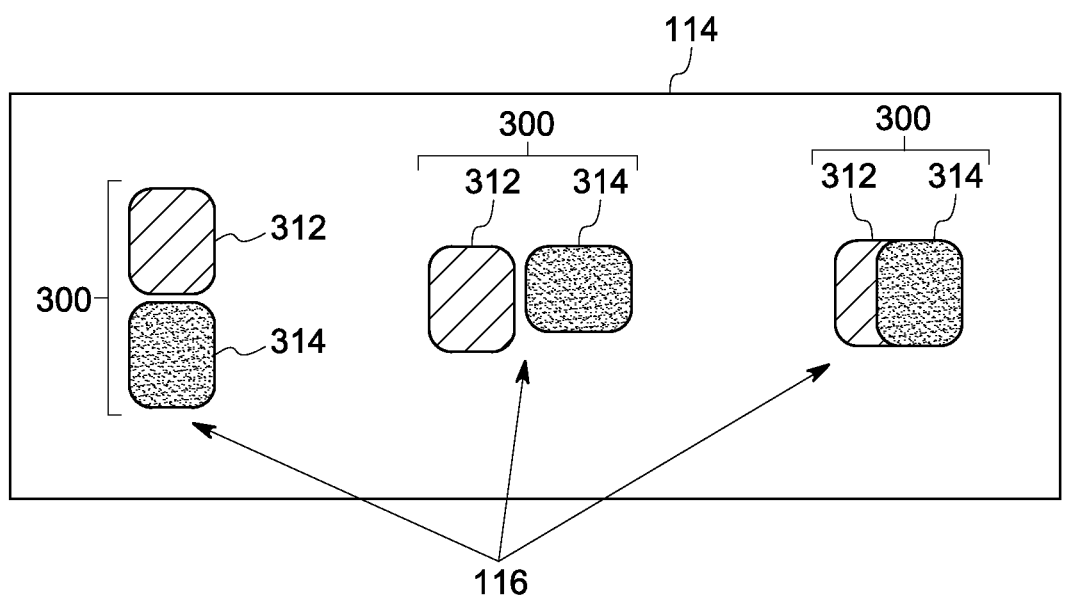
FIG. 3 is a schematic illustrating a plurality of image pattern pairs that may be used with the creep monitoring system shown in FIG. 1.

In one embodiment of the present invention, a method of monitoring and measuring creep in an object 114 is disclosed. According to this method, instead of one image pattern for measuring the creep, the creep sensor assembly 116 includes an image pattern pair 300 disposed on a surface of the object 114 as shown in FIG. 3. As used herein, an "image pattern pair" is a group of at least two image patterns. As used in this application, an image pattern pair 300 is exemplified as a pair of two image patterns: first image pattern (alternately first pattern) 312 and second image pattern (alternately second pattern) 314 as shown in FIG. 3, even though in reality an image pattern "pair" may have more than two image patterns depending on different embodiments that may cater to complex parameters of the object 114 that need to be measured and compared.

The first pattern 312 and second pattern 314 of the image pattern pair 300 are placed on a surface of the object, either placed adjacent to each other, or partially or fully overlapped with each other so that each pattern 312 and 314 substantially registers the changes happening at that particular part of the object 114. This layout of image pattern pair 300 having adjacent or overlapping first pattern 312 and second pattern 314 is clearly different from having multiple creep sensor assemblies 116 (as shown in FIG. 3) that may be deposited on the object surface at multiple locations for local creep detection. In this embodiment, the optical monitoring system 210 (FIG. 2) is in line of sight to the image pattern pair 300 and configured to collect information regarding observed creep and also an offset of the creep sensor assembly 116.

As used herein an "offset" of the creep sensor assembly 116 includes different factors that potentially affect the accuracy of the creep determination. Some non-limiting examples for the causes of offset are described below. The offset may result from a small change in the standoff distance of the optical monitoring system 210 with respect to the object 114 during the measurement, wherein the change in the standoff distance is so small that the operator might not account for the magnification change that result from the change in the standoff distance. Similarly, a small tilt in the optical monitoring system from the ideal angle for recording may introduce an error in the creep measurement, which may be accepted as the correct creep measurement. In one embodiment, if the sensor that records the final pattern and thus creates the moiré pattern is replaced with a new sensor, a small change in the calibration of the new sensor would introduce errors in the creep measurement. In another embodiment, if the overall part (of the object 114) gets heated up and hence the part expands uniformly, the creep sensor assembly 116 may pick up the magnification as a part of the one-directional creep rather than accounting as an overall magnification change.

Embodiments of this invention involve adding other patterns (such as, second pattern 314) to the originally printed pattern 312 on the part, thus enabling the system to compensate for the standoff distance, tilt, or calibration of the sensor as well as other factors that might change the magnifications of the pattern as seen by the optical monitoring system. This correction makes the system highly robust to small setup errors when reading the pattern, thus improving the accuracy of the reading.

Figure 4:
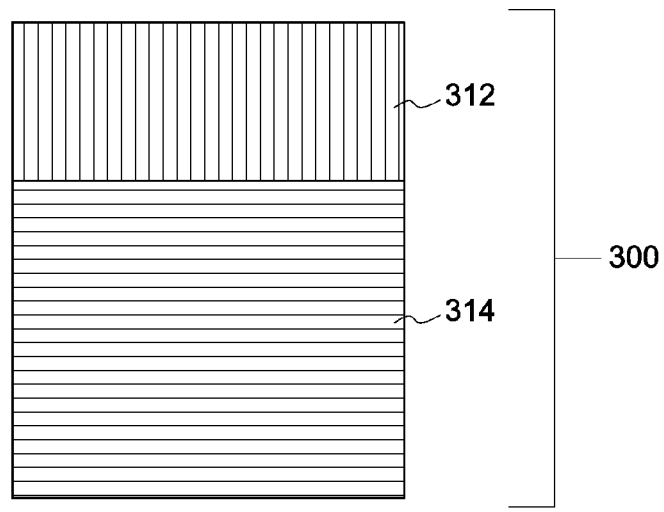
FIG. 4 is a schematic of an exemplary image pattern pair, in accordance with an exemplary embodiment of the present invention.

The image pattern pair 300 may include different combinations of first pattern 312 and second pattern 314. In one embodiment, the first pattern 312 is a periodic grating and the second pattern 314 is another periodic pattern that is disposed at a finite angle relative to the first pattern. In one particular embodiment, the second pattern 314 is positioned adjacent to, and oriented perpendicular to, the first pattern 312 as shown in FIG. 4. Non limiting examples for other image pattern pairs 300 include first pattern 312 and second pattern 314 at an angle (including perpendicular), and overlaid on one another, a second pattern 314 that is made to reflect at different color or lighting from the first pattern 312 either adjacent or overlaid, or a second pattern 314 with a different frequency from the first pattern 312 but oriented the same way either overlaid or adjacent to first pattern 312.

The use of image pattern pair 300 in identifying the errors in creep measurement is explained below using the exemplary pattern pair of FIG. 4. In this example, a first pattern 312 that is used to measure the strain is placed with a particular pattern having the gratings perpendicular to the direction of expected strain of the part surface 114 when the part 114 undergoes a rotational motion. During the rotational movement of the part 114, frequency of the gratings may change as a result of creep formation tangential to the rotational direction. When an image of this changed frequency pattern is compared with the originally captured frequency pattern, the relative change in frequency of the first pattern 312, in comparison with an original frequency of the first pattern 312 would provide the information regarding the observed creep. In one embodiment, a moiré pattern that emerges by the comparison of the first pattern 312 before and after the creep would be used to find out the creep occurred at the surface region of part 114, where the pattern 312 is present. Thus, the first pattern 312 is used to receive information from the creep assembly 116 regarding an observed creep associated with the object 114. However, if there is any change in that region of surface of the part 114, or any change in the image captured by the sensors of the optical monitoring system that is not an outcome of the creep of the surface region of the part 114, the moiré pattern may still erroneously identify that change as a result of creep.

Considering a second pattern 314 oriented perpendicular, and placed adjacent to the first pattern 312, any change in that surface region of the part 114, or change in the image captured by the sensors due to any reason other than the creep resulting from rotational movement, would be captured in the second moiré pattern corresponding to the gratings pattern 314. The moiré pattern of the second pattern 314 would not include any effect of the creep, since the gratings are not patterned in the direction of the rotation and hence should not see strain as the part is assumed to only be stretching in one direction. Therefore, by reading the new pattern also against a reference grating in the sensor (also perpendicular to the original reference), a moiré pattern is produced that can be read by the same analysis as the original pattern. This analysis may be Fourier analysis, fringe counting, or phase shift methods. The change in this adjacent pattern should only be due to other changes (than creep), caused by for example, a change in distance, a change in angle of the view to the surface, or a change due to environmental differences such as elevated temperatures that may cause the whole part to change uniformly (therefore not a surface strain of interest). Thus, the second pattern 314 is used to receive information from the creep assembly 116 regarding an offset of the creep sensor assembly. Hence, by accounting for the errors captured by the second pattern 314 in the creep calculated using the first pattern 312, one may correct the observed creep and determine actual creep of the surface region of the part 114. Since the patterns 312 and 314 are placed adjacent to each other, the corrections would substantially correspond to the surface region that has the first and second patterns printed thereon. The information regarding the offset of the creep sensor assembly 116 may also be obtained from a comparison of relative change in frequency of first 312 and second 314 patterns.

Figure 5:
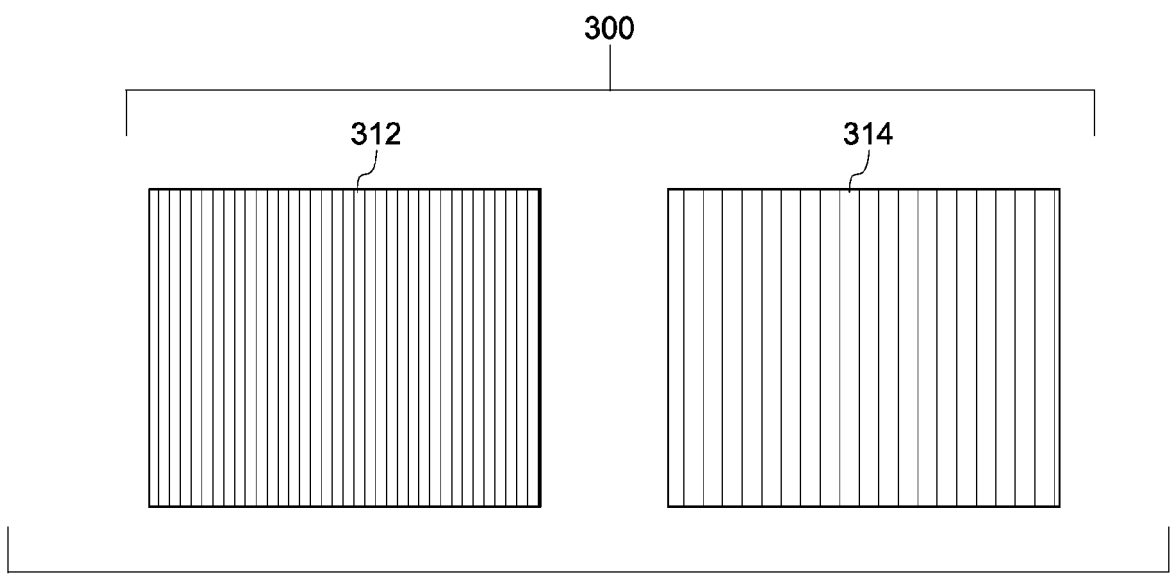
FIG. 5 is a schematic of an exemplary image pattern pair, in accordance with an exemplary embodiment of the present invention.

FIG. 5 depicts another image pair 300 using a different frequency pattern 314 relative to the original pattern 312, but with the same orientation as the original pattern 312 that is used to measure strain or creep. The image patterns 312 and 314 with different spatial frequencies are placed in the expected direction of creep and may be overlapped or placed adjacent to each other. The two patterns 312 and 314 may produce two moiré patterns, one of which will be finer that the other, depending on the frequency of the original grating patterns before the creep. Since the frequencies of the original gratings were different, the effect of magnification on the two resultant moiré patterns also would change as a percent of the original difference between the grating patterns 312 and 314. This small difference between the moiré patterns can be used to calculate the overall change in magnification of the two patterns. Additionally, each pattern 312, 314 individually will also show the strain of interest. This method allows the full usable or viewable region to be used for both the strain measurement and for correcting the magnification errors due to setup or environment, rather than one area being used for one purpose and an adjacent area for another.

Thus, the method of monitoring creep in the object 114 includes monitoring the creep sensor assembly 116, which includes monitoring the image pattern pair 300 on the surface of the object 114. The information about the observed creep and the offset may be obtained from monitoring the image pattern pair and receiving information regarding the changes happened in the image pattern pair 300. The method further includes correcting the observed creep using the information regarding the offset and outputting the corrected information relative to creep.

For any of the method described above, the grating patterns 312 and 314 could be encoded using such effects as color, fluorescence, or unique structures (such as waves in the lines) to be different from each other so as to be easily distinguished from each other. These methods of encoding would potentially permit both patterns to be overlaid in the same space without interfering with each other (rather than adjacent). The use of color cameras or separate encoded gratings would permit the patterns to be read either sequentially or simultaneously.

By introducing capability for correction into the sensor assembly through the use of pattern pair 300, the system described herein may demonstrate improved robustness and accuracy, because the alignment and standoff of the sensor may be less critical to obtain an accurate reading, when compared to that of a single pattern reading.

The system and method of measuring accurate creep as disclosed in the above embodiments may be used for static as well as dynamic measurements. As used herein "static measurement" refers to the measurements that are performed at a substantially short period after a change in the object 114 occurred. A "dynamic measurement" may be the measurement that is performed when the object 114 is still in movement without substantial intentional delay.

The above-described embodiments of a method and system of measuring the observed creep, measuring the offset, and correcting the observed creep to determine the actual creep, provides a cost-effective and reliable means for providing a lifing prediction for moving objects while in service. As a result, the method and system described herein facilitate managing machinery assets in a cost-effective and reliable manner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of monitoring creep in an object, comprising:
monitoring a creep sensor assembly comprising an image pattern pair disposed on a surface of the object, wherein the image pattern pair comprises a first pattern and a second pattern;
receiving information from the creep sensor assembly regarding an observed creep associated with the object;
receiving information from the creep sensor assembly regarding an offset of the creep sensor assembly obtained from a comparison of relative change in frequency of the first and second patterns;
correcting the observed creep using the information regarding the offset, and
outputting the corrected information relative to creep.

2. The method of claim 1, wherein the information regarding the observed creep is obtained from a relative change in frequency of the first pattern, in comparison with an original frequency of the first pattern.

3. The method of claim 1, wherein the offset of the creep sensor assembly is relative to the object.

4. The method of claim 1, wherein a second pattern is at an angle to the first pattern.

5. The method of claim 4, wherein the second pattern is perpendicular to the first pattern.

6. The method of claim 1, wherein the second pattern has a different spatial frequency as compared to the first pattern.

7. The method of claim 1, wherein the second pattern has a different color as compared to the first pattern.

8. The method of claim 1, wherein the second pattern is adjacent to the first pattern.

9. The method of claim 1, wherein the second pattern is overlaid on the first pattern.

10. A creep monitoring system comprising:
   a creep sensor assembly comprising:
      an image pattern pair disposed on a surface of an object, wherein the image pattern pair comprises a first pattern and a second pattern;
      an optical monitoring system with line of sight to said image pattern pair, said optical monitoring system configured to collect information regarding observed creep and an offset of said creep sensor assembly; and
   a processor configured to:
      receive the information regarding the observed creep and the offset; and
      determine a corrected information relative to creep, wherein the information regarding the offset is obtained from a relative change in frequency of the second pattern, in comparison with an original frequency of the second pattern.

11. The system of claim 10, wherein the second pattern is at an angle to the first pattern.

12. The system of claim 11, wherein the second pattern is perpendicular to the first pattern.

13. The system of claim 10, wherein the second pattern has a different spatial frequency as compared to the first pattern.

14. The system of claim 10, wherein the second pattern has a different color as compared to the first pattern.

15. The system of claim 10, wherein the second pattern is adjacent to the first pattern.

16. The system of claim 10, wherein the second pattern is overlaid on the first pattern.

* * * * *